United States Patent
Turner

[11] 4,075,178
[45] Feb. 21, 1978

[54] ORGANOALUMINUM COMPOSITIONS

[75] Inventor: John Harry Wallice Turner, Chapel-en-le-Firth, England

[73] Assignee: Manchem, Limited, London, England

[21] Appl. No.: 620,239

[22] Filed: Oct. 6, 1975

Related U.S. Application Data

[63] Continuation-in-part of Ser. No. 345,377, March 27, 1973, abandoned.

[30] Foreign Application Priority Data

Mar. 28, 1972  United Kingdom ............... 14390/72

[51] Int. Cl.² ............................................. C08G 63/76
[52] U.S. Cl. ............................... 260/75 T; 260/22 T; 260/2 M; 260/59 R; 260/46.5 E; 260/47 EP; 260/448 R; 260/448 AD
[58] Field of Search ....... 260/448 R, 448 A, 448 AD, 260/448 B, 448 C, 75 T, 78 SC, 2 M, 22 T, 46.5 E; 526/27, 30, 48

[56] References Cited

U.S. PATENT DOCUMENTS

| | | | |
|---|---|---|---|
| 3,175,996 | 3/1965 | Gregorian | 526/48 |
| 3,361,845 | 1/1968 | Watanabe | 260/75 T |
| 3,375,235 | 3/1968 | D'Alelio | 526/48 |
| 3,458,462 | 7/1969 | Hostetler | 526/48 |
| 3,476,532 | 11/1969 | Hartman | 526/48 |
| 3,531,417 | 9/1970 | Morehouse | 260/448 R |
| 3,531,507 | 9/1970 | Morehouse | 260/448 R |
| 3,779,952 | 12/1973 | Leonard | 526/48 |
| 3,845,028 | 10/1974 | Bethea | 526/48 |

*Primary Examiner*—Paul R. Michl
*Attorney, Agent, or Firm*—James R. Thornton

[57] ABSTRACT

Organoaluminum compounds of the formula

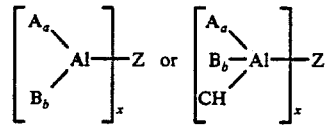

in which A, B and C are each selected from alkoxy, aryloxy, alkylcarboxyl, arylcarboxyl, a dicarboxylic acid half ester, a dicarboxylic acid half amide, alkyl sulfate, aryl sulfonate, dialkyl phosphate, alkylaryl phosphate, diaryl phosphate, dialkylphosphite, alkylaryl phosphite, diarylphosphite, or oxymetal group of the formula OMA in which M is a divalent metal; $a$ and $b$ are 0, 1 or 2 with the proviso that $a + b = 2$; $x$ is at least 2 and $z$ is a polyfunctional group selected from organic polymers or polycondensation products, inorganic macromolecules and metals. The products are prepared by addition of a polyfunctional compound or metal to an excess of organoaluminum compound.

14 Claims, No Drawings

ORGANOALUMINUM COMPOSITIONS

This is a continuation-in-part of my copending application Ser. No. 345,377 filed Mar. 27, 1973, now abandoned.

The present invention relates to substituted aluminum compounds containing organic groups which can be used in the preparation of useful industrial coatings, binding agents and molding compositions and to the method of preparation of said substituted aluminum compounds.

The use as additives to paints and printing inks of aluminum-organic compounds such as the alkoxides, their direct derivatives by substitution, and the less directly derived oxoaluminum acyloxides, is known. The aluminum alkoxides, when added to an alkyd resin, cause an increase in structure of the medium by their reacting with hydroxyl, carboxyl and other reactive groups available in the alkyd molecule such as hydroperoxides and active methylene in the manner shown in Reaction 1.

Reaction 1

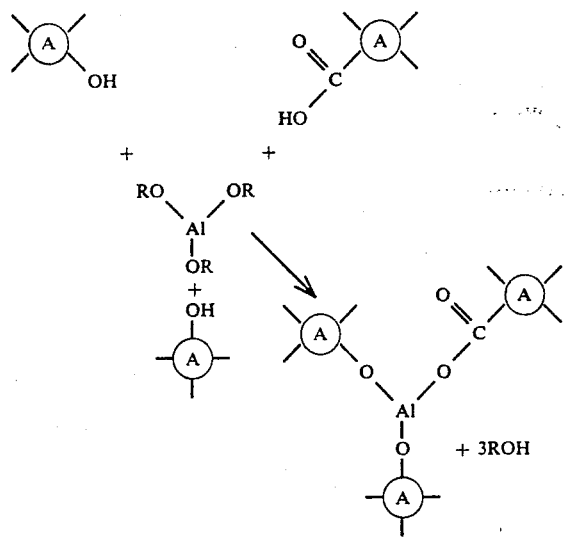

A small amount of such a complex has a marked effect on the mobility of the media, and hence very little aluminum alkoxide (1%) has a marked increase in the structure of the medium.

While small amounts of aluminum compounds are sufficient to affect in a beneficial way the structure of the paint or ink to which they are added, they have no major effect on the other properties of the coating or ink. Larger additions have hitherto been unacceptable because of the difficulty in applying highly structured paints and the undesirability of excessive thinning necessary to counteract the effect of structuring. On the other hand, instead of being used as an additive to structure a drying oil or resinous medium, the oxoaluminum compound can be used successfully as the sole non-volatile component of surface coatings for some applications. For example, oxoaluminum stearate is widely used for the treatment of masonry, timber and other porous materials to make them water repellent. It is readily soluble in non-polar solvents and as a 60% solution in white spirit, has a viscosity of approximately 2 poises. However, when diluted further and applied, water in the atmosphere or in the substrate adds on to the oxoaluminum compound, forming the dihydroxy compound which associates to the characteristic water repellent gel.

Reaction 2

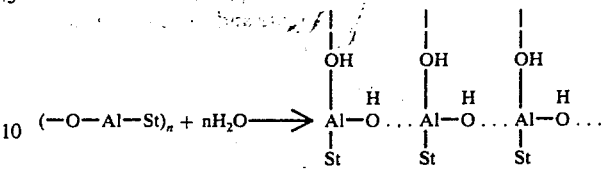

The foregoing reaction between aluminum compounds, such as the alkoxides, and coating media, as for example, the long oil air drying alkyd resins, have always involved a reaction whereby the aluminum compound is added to the other polyfunctional reactant.

It has been found that when a polyfunctional reactant is added to an excess of an aluminum compound having at least one organic group through which reaction with the functional group on the polyfunctional reactant may be effected, cross-linking does not occur because each molecule of the aluminum compound is substituted by no more than one of the functional groups present in the polyfunctional reactant. The reaction product will then be of the nature represented diagrammatically in Reaction 3.

Reaction 3

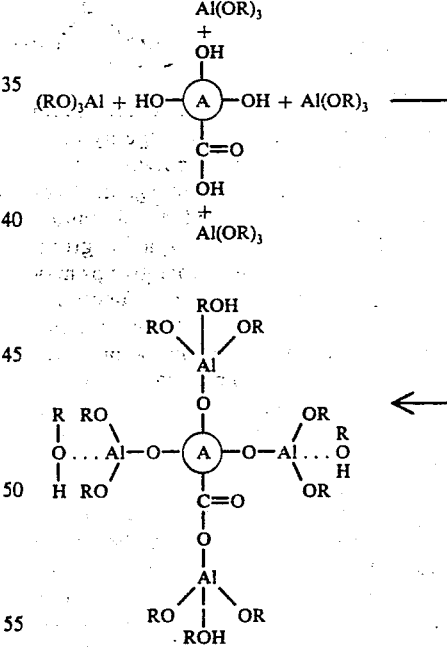

The polyfunctional reactant is an organic polymer or organic polycondensation product, an inorganic macromolecule, or a metallic particle having at least two functional groups each capable of reacting with at least one of the organic groups on the aluminum compound. The products from the reaction represent a major advance in surface coating technology.

The substitution groups attached to the aluminum are chosen to protect the aluminum compound against viscosity increase as a result of association by coordination. Thus, the aluminumpolyfunctional reactant complex remains stable on storage. However, if the complex is exposed to conditions which permit the replacement of one or more of the sterically protecting radicals by substituents, notably the hydroxyl group, it has been found that the reduction of steric protection allows the aluminum compound to associate and the liquid product is converted to a gel structure.

Reaction 4

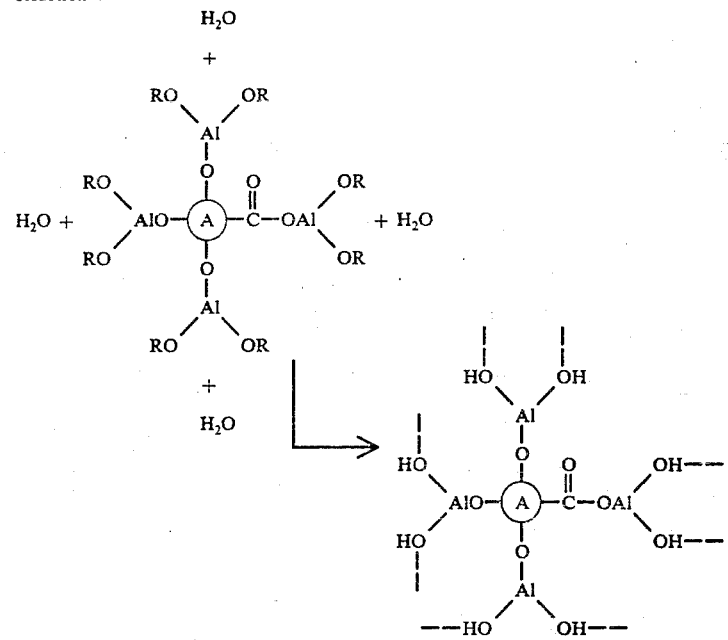

It is possible, therefore, to make a fluid aluminum containing medium which is stable on storage by reaction between a polyfunctional organic polymer or organic polycondensation compound, an inorganic macromolecule, or a metallic particle and an aluminum compound containing at least one organic group through which reaction with the functional groups may be effected, characterized in that the polyfunctional compound is added to an excess of the aluminum compound. The reaction may be carried out in the presence of a solvent or without solvent. The product of the reaction is sensitive to water which causes gellation to take place. Thus, when the product is applied as a film, the film will gel through reaction with atmospheric moisture or moisture in the substrate. If the aluminum compound employed is an aluminum trialkoxide and the product is applied as a film, the rate of reaction with water and resultant gelation may be greater than the rate at which the alcohol by-products of reaction and solvent can escape from the film. This results in subsequent shrinkage and the film integrity is impaired. It has been found that this sensitivity to moisture and, thereafter of gelation rate, can be controlled by substituting one or more of the alkoxide groups attached to the aluminum by a group having greater steric impedence and/or lower volatility than the alkoxide group. Substituents such as rosin; versatic acid and other suitable branched chain carboxylic acid; alkyl, aryl and halogenated phenols and highly branched chain alcohols of low volatility can all be beneficial in this respect and the choice of which to use depends as much upon film performance after drying as on behavior during the drying stage.

Thus, the present invention provides stable fluid compounds of the formula

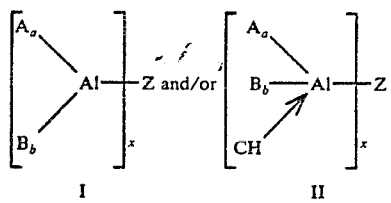

in which A, B and C may be the same or different and may be selected from alkoxy, substituted alkoxy, aryloxy, substituted aryloxy, alkylcarboxyl, substituted alkylcarboxyl, arylcarboxyl, substituted arylcarboxyl, a derivative of a dicarboxylic acid having only one carboxyl group available for bonding directly to aluminum (e.g. half ester or half amide), alkyl sulphate, aryl sulphonate, dialkyl phosphate, alkylaryl phosphate, diarylphosphate, dialkyl phosphite, alkylaryl phosphite, diarylphosphite, or an oxometal group of the formula OMA in which O is an oxygen atom, M a divalent metal and A is as hereinbefore defined, and H is a hydrogen atom. Additionally, $a$ and $b$ may be 0, 1 or 2 with the proviso that $a + b = 2$. Z is an organic polymer or organic polycondensation compound, an inorganic macromolecule or metallic particle derived from $ZH_x$ as defined below in which $x$ is greater or equal to 2.

The stable fluid compounds I and/or II of this invention may be prepared by the addition of a compound $ZH_x$ either alone or in a solvent to an excess of an organic aluminum compound of the formula

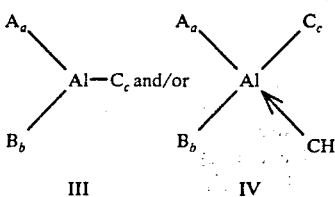

III  IV either alone or in a solvent, where $ZH_x$ is an organic polymer or organic polycondensation product, an inorganic macromolecule or a metallic particle containing at least two reactive hydrogen atoms (H) capable of reaction through C in formula III or formula IV and $x$ is greater or equal to 2, and $c$ may be 1, 2, or 3 with the proviso that $a + b + c = 3$, and A, B and C are as hereinbefore defined. In a preferred embodiment of the invention, H is a reactive hydrogen atom associated with a hydroxyl, carboxyl, hydroperoxide or an active methylane group in an organic polymer or organic polycondensation product or, in the case of an inorganic macromolecule or metallic particle, H is on a reactive hydrogen atom associated with a surface hydroxyl group and/or a hydroxyl group which forms part of a water molecule adsorbed on to the surface of the inorganic macromolecule or metallic particle.

Formula II and formula IV are also intended to include the acidic forms V and VI which may, under some conditions, exist in equilibrium with the undissociated forms. This equilibrium may be represented as follows.

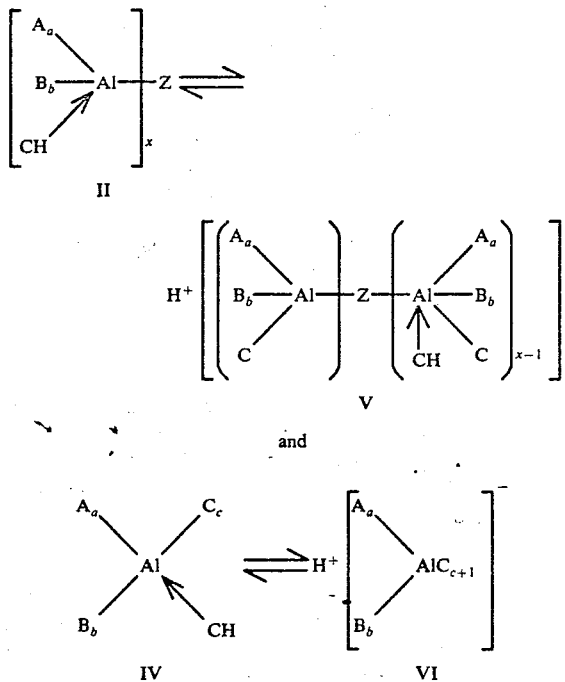

II

V and

IV  VI

In a further embodiment of the invention, the group C may be isopropoxy, sec butoxy and ethoxyethoxy.

In a preferred embodiment, the invention provides a composite medium comprising a substituted aluminum alkoxide as hereinbefore defined, an alkyd resin including saturated and unsaturated polyesters of the linear type, phenolic resins, raw, oxidized and polymerized drying oils, other resinous materials which have reactive groups and which are capable of replacing groups on aluminum alkoxides and their derivatives as hereinbefore defined such as polyepoxides and silicone resins.

The aluminium compounds are modified alkoxides and they can be combined with a resin by using reactive groups, mainly hydroxyl and carboxyl, in the resin to substitute labile groups in the aluminum compound. The preferred labile groups C are residual isopropoxides and, by adding the resin to the solution of the aluminum compound with sufficient agitation and in amount less than would result in the aluminum compound being substituted by more than one reactive group on the macromolecule or metallic particle $ZH_x$ it is possible to avoid cross-linking reactions which cause thickening and gelation. The products prepared in this way are quite stable when stored out of contact with moisture but on application and exposure to conditions which make possible the replacement of the steric protective groups by an hydroxyl radical, gelation by coordination occurs rapidly and results in its conversion from the liquid to the gel state.

Additionally, the substituent groups may be used to modify the compatibility of the aluminum compounds with other materials and to contribute other specific properties to the composition in which it is used. For example, pentachlorophenate contributes powerful biocidal activity to compositions in which it is incorporated; the versatate radical enhances water and alkali resistance; the half phthalate ester contributes toughness and pale color, while the half maleate ester introduces a copolymerization capability useful in polyester and some rubber compounding applications.

By combining the aluminum compounds with pigments or fillers such as titanium dioxide, china clay, blanc fix and such coloring pigments as Prussian blue, phthalocyanines or iron oxide, it is possible to obtain paints such as quick drying primers for wood and chip board, which are easily applied, are effective sealants and dry quickly to provide a sound non-toxic base to which other coatings will adhere well.

When combining the aluminum compounds with pigments, there is the possibility of water which may cause premature hydrolysis of the compound in which the pigment is dispersed. Although pigments may be dried in an oven, it is generally more satisfactory to scavenge any free water by dispersing the wet pigment in a solvent such as white spirit or other acceptable diluent (e.g. alcohols, ketones, esters and ethers) containing sufficient aluminum alkoxide to react with the water. This not only eliminates the water but also deflocculates most pigments and thereby facilitates their milling.

Combined water in the form of a chemically bound hydroxyl group is thought to provide the means of chemically associating the pigment with the aluminum compound in which it is dispersed. This association has been shown to confer a strong affinity between pigments and the dispersive medium shown in the wetting action of the medium for pigments and also for the notable mechanical reinforcement apparent in pigmented aluminum compound.

The aluminum compounds can also be associated in this way with materials other than pigments, for example, non-metallic oxides or hydroxides such as silica; metallic oxides such as titanium dioxide, iron oxides, cuprous oxide, red lead or litharge; metallic salts such as lead chromate, zinc borate, basic lead carbonate, basic lead sulphate, zinc phosphate and zinc chromate; metals or alloys such as aluminum, zinc or copper; non-metals such as carbon and minerals such as china clay, zirconia, asbestos, titania or vermiculite in which the reactive hydrogen atoms are provided by surface hydroxyl groups or by water physically bound to the surface.

This association has been shown to confer a strong affinity between the fillers such as precipitated silica, which is known to combine high surface area with high hydroxyl content.

The moisture setting principle can be used in the formulation of surface coatings for many applications which involve a variety of application techniques. The pigmented or filled aluminum compounds, effectively seal porous materials such as hard board, chipboard and asbestos cement sheet.

Road marking paints containing pigments which will combine with the aluminum compound also provide a good example of the combined benefits arising from high setting speed, resistance to bleeding when applied to tar or asphalt surfaces and the good mechanical properties arising from the chemical association between the pigment and/or filler and the aluminum compounds in which they are dispersed.

Road marking paints can be formulated for application by pneumatic applicator and rapid set by atmosphere moisture or water in the substrate followed by a hardening, polymerization stage. The metal/organic matrix impedes bleeding and tends to maximize pigment opacity and brightness.

The aluminum compounds can be used in the foundry industry as core binding agents, core oils and in hot box or shell molding. It has been concluded that hardening involves both the conventional process of oxidation-polymerization in the case of drying oil modified binder or polycondensation in the case of phenolic resin binder and the superimposed coordinate association of the aluminum complex which involves association also with reactive groups on the surface of the sand particle. By incorporating aluminum monoisopropoxide monoversatate mono(monoisopropyl) maleate into rubber compounds using as fillers a reactive silica such as Ultrasil VN3, it has been found possible to enhance to a significant extent such physical properties as modulus tensile strength, resilience, and abrasion resistance.

Composite media, in which the aluminum compounds are combined with alkyds of shorter oil length, possess the quick set and solvent release characteristics of conventional hard resin based gravure inks, and reduce dependence on rosin based resins.

Other applications of these high aluminum compositions are in paints for coating pipes and for insulating and sealing, as well as in marine paints to line tanks and prevent fouling and corrosion and paints for use in the car and rolling stock industries. The compositions can also be used to provide architectural finishes and to preserve and seal wood, particle board and hardboard and to render them flame-proof. These high aluminum compositions can be used where polyester resins or epoxide resins are used at present, i.e. as body fillers, pipe seals, insulated varnishes, surface coatings, adhesives, laminates and floorings. The compositions can also be used as binders or friction modifiers in brake linings and clutch facings and as phenolic mouldings, grinding wheels and laminates.

Composite media prepared with the compounds of the present invention have a better drying rate and greater hardness as well as improved water resistance and enhanced dimensional stability. This is of particular value in the formation of coatings for wood which are required to combine fungicidal properties on the one hand, with water repellent or sealing properties on the other.

In one embodiment a sealing composition for use in protecting cellulosic materials from fungal attack and for conferring water repellency properties on the material is provided, which composition is prepared by the reaction between aluminum alkoxide and a phenol. The alcohol liberated may, if desired, be removed by distillation, or may be retained as one of the solvents for the mixed aluminum alkoxide/phenoxide. Preferably from 0.5 to 2.0 mols of phenol are used for each mol of aluminum alkoxide. If now the aluminum alkoxide/phenoxide, preferably diluted by the addition of suitable solvents which include hydrocarbons, chlorinated hydrocarbons and higher alcohols such as butanol, the monoethyl ether of ethylene glycol, cyclohexanol and the oxoalcohols of the C7/C9 range, is blended with an air-drying oil modified alkyd resin of the type commonly employed in gloss paints media, it is found that mixed solutions can be obtained which remain liquid on prolonged storage. Mixtures of unmodified aluminum alkoxides with the same alkyd resins at the same aluminum content and resin concentration level are, in the same circumstances, much less stable and are liable to gel before they can be applied. With the addition of some paint driers, these blends of aluminum alkoxide/phenoxide with alkyd resins, can be applied to wood surfaces to form coatings which dry hard, seal the surface and are strongly fungicidal. Alternatively, they can be pigmented to make them suitable for use as wood primers, sealing the substrate to which they are applied, conferring fungicidal properties and providing a sound surface on to which further coatings of paint can be applied.

In a further embodiment a product comprising the phenol substituted aluminum alkoxide which has been modified further by substitution reaction with a carboxylic acid is provided. For example, 0.0 to 1.5 mols of carboxylic acid are reacted with the mixed aluminum alkoxide/phenoxide containing in combined form 0.5 to 2.0 mols of phenol. The reaction is effected, preferably by heating the carboxylic acid with the aluminum/phenoxide under reflux conditions. The liberated alcohol may be removed by distillation at atmospheric pressure or under vacuum, or it may be left to serve as a solvent/diluent for the mixed aluminum/phenoxide carboxylate. In this case, it may be necessary further to dilute the product with other solvents which include hydrocarbons and higher alcohols in order to achieve a satisfactory solvent balance and solvating power for the compound.

The resultant product, when applied to cellulosic materials and the residual alkoxide groups hydrolyzed, renders the cellulosic material resistant to fungicidal attack, and at the same time provides a satisfactory water repellent treatment. Normally, the hydrolysis of the residual alkoxy groups occurs as a result of reaction with water in the substrate and atmospheric moisture, but it may, if desired, be accelerated by treatment with water after application.

Products with, or preferably without modification by reaction with carboxylic acids, are particularly suitable for incorporation as components of primer/sealers for cellulosic structural materials such as wood, particle or chipboard, fiberboard, or plywood, and may be applied by conventional means. After application it is thought that water in the substrate or hydroxyl groups which form part of the cellulose molecule may react with the aluminum phenate progressively releasing the phenol, which by the process of diffusion, may penetrate more deeply into the cellulosic material, and enabling the aluminum atom to complex both with the medium in which it is incorporated, and with the substrate to which it is applied. Such complexing reactions have been observed to reinforce alkyd and other paint media and enhance their adhesion to polar substrates.

Cellulosic textile materials, ropes, matting and the like, may also be rendered water repellent and resistant to fungal attack by these compositions, which are preferably applied by conventional techniques. If desired, other materials, such as fire retardants and coloring matter, may be incorporated into the solutions into which the cellulosic materials are dipped. The compositions of the invention can also be diluted with chlorinated solvents, such as trichlorethylene, which, in dipping compositions, has the advantage of providing a heavy vapor barrier over the surface of the solution in the dip tank, thereby providing protection against hydrolysis by atmospheric moisture. In addition, the use of a chlorinated solvent of high volatility results in a rapid rate of air-drying.

In a comparison of a pigmented resinous medium with a composite aluminized medium of this invention, both pigmented to the same level showed that, with respect to color and opacity, the aluminized medium conferred advantages over the unmodified resin. It would appear that this may be due to a reduced tendency of the pigment to flocculate when dispersed in the composite medium.

Such aluminized resin media are soluble in most non-polar solvents. Trichlorethylene may be preferred for use as the principal solvent in air-drying aluminized alkyd coatings (used for wood or metal and applied by dipping) because of its good solvent power and high vapor pressure of the dense vapor at ambient temperatures and thereby acting as a vapor barrier over the dip tank and effectively protecting against hydrolysis in the tank. Rapid volatilization of the trichlorethylene from the paint film after dipping, ensures a good balance of gelation rate to solvent evaporation.

Mineral oils, aromatic extracts, liquid butene and other olefenic polymers and such chlorinated hydrocarbons as chlorinated paraffin wax and chlorinated diphenyl make possible the production of "solventless" coatings and inks.

Although not strictly classifiable as "non-reactive," esters of drying and semi-drying oil fatty acids can also be employed as non-volatile solvents during the first stage of drying and have the added advantage of integrating into the metal organic composite by co-polymerization in the second stage of the drying process.

A primary objective in formulating the types of aluminized media which have been described is to obtain in a single coating the combined benefits of quick gel formation by coordination and subsequent irreversible covalent polymerization from a medium which under sealed storage conditions has prolonged stability. The gelation by coordination is induced by the hydrolytic action of moisture in the atmosphere or in the substrate; the covalent polymerization follows the usual route of air oxidation and free radical promotion catalyzed by the usual paint driers. Secondary objectives are to modify in a beneficial way specific physical and chemical characteristics of the applied film. By the appropriate compositional variations within the framework necessary to achieve these objectives it is possible to formulate compositions for a wider variety of applications, some of which are exemplified below.

The effect of hydrolysis by water in the atmosphere or in the substrate on the aluminum medium is manifested rapidly by the change in structure which occurs. This tends to make impractical the brush application of these aluminized media. On the other hand, the combination of quick set characteristics with higher solids content benefits their application by airless spray to give thick films with higher resistance to sagging and good through hardening properties. For this reason aluminized alkyds are ideal for industrial paints which can be applied by spray and are required to air-dry quickly and thoroughly when applied in greater than normal film thickness.

The sensitivity of the paints described to the effect of moisture in the atmosphere and in the substrate is a limiting factor in the design of coatings for dipping but tri-chlorethylene as a solvent combines the need for vapor blanketing against hydrolysis of the aluminized paint in the dip tank with the achievement of solvent evaporation before water initiated gelation of the applied film is too far advanced. The rapid air drying rate of trichlorethylene thinned aluminized alkyd media is of benefit in the formulation of primers and finishes for factory made joinery and cellulosic materials generally.

The invention is further illustrated by the following Examples.

EXAMPLES 1-9

A series of experiments in which substituted alkoxides were mixed with the same alkyds and subjected to storage stability tests confirmed that the critical causative factor in gelation is the ratio of aluminum metal to the alkyd, while the rate determining factors appear to be the concentration of the two reactants in non-reactive diluents and the steric geometry of the substituent groups attached to the aluminum atom.

TABLE I

|  | 1 | 2 | 3 | 4 | 5 | 6 | 7 | 8 | 9 |
|---|---|---|---|---|---|---|---|---|---|
| EPOK A1061/50 WS | 100 | 100 | 100 | 100 | 100 | 100 | 100 | 100 | 100 |
| Isopropoxy aluminum diversatate (90% solids) | 0 | 1 | 2 | 4 | 8 | 16 | 32 | 64 | 96 |
| Gel time (days) | stable | stable | >21 | 21 | 14 | 7 | 5 | >21 | stable |
| Drying time* (hours) | 42+ | 42+ | 42 | 32 | 29 | 14 | 7.5 | 4 | 3.5 |
| Hardness*, (1) | 18 | 20 | 21 | 22 | 23 | 23 | 32 | 36 | 39 |
| (11) | 18 | 20 | 18 | 20 | 22 | 19 | 21 | 21 | 29 |

TABLE I-continued

|  | 1 | 2 | 3 | 4 | 5 | 6 | 7 | 8 | 9 |
|---|---|---|---|---|---|---|---|---|---|
| Appearance (X) | Iridescent → | | | | | | | | Clear |

*Drying time measured at point of no detectable scratch on B-K recorder.
Film thickness (wet) - 3 thousand inch: Temperature - 15° C.
Drier content - 0.06% Cobalt; 0.5% Lead based on alkyd solids.
*, Hardness measured by Sward Rocker. Glass plate value 90.
(I) Measured 4 days after application.
(II) Measured 15 days after immersion in sea water.
(X) Appearance observed immediately after 7 days immersion in sea water.

The effect of varying the ratio of a suitably substituted aluminum alkoxide to the alkyd on the drying rate of the medium and the proportion of the applied film is exemplified in Table 1. In this case the aluminum compound used was aluminum monoisopropoxide diversatate and the alkyd was the proprietary resin Epok A.1060/75 reduced with white spirit to 50% non-volatile content. The ratio of aluminum to alkyd range from well below the minimum aluminum content necessary for stability to a little above. The first points to note in the comparison of this series are the progressive improvements in drying rate, hardness and film built through increased solids, which has been achieved through the introduction of this particular aluminum compound. It is interesting to note too, that in Example 9, the versatate radical accounts for 60% of the dried film weight and aluminum, as metal, 4.5%. As a pointer, perhaps to the durability of this type of metal/organic coating, the behaviour of the film on immersion in sea water shows a progressive improvement with increasing content of aluminum versatate. Although after 4 weeks immersion in sea water, the rocker hardness of example 9 had diminished from 39 to 29, it still remained substantially harder than the unmodified alkyd resin. In other respects, notably in gloss, clarity and dimensional stability, 9 was outstanding compared with the unmodified alkyd film and clearly better than other composite films in the series.

The precise, physico-chemical nature of the association between the aluminum and the other components of the dried film remains to be elucidated, but it is thought possible that the aluminum is associated on the one hand with the two versatate radicals and on the other with such polar groups in the alkyd as are available to complete the shell of six oxygens with which the aluminum is surrounded in its most stable association. The practical evidence of a close association between the two components is considerable and includes improved solvent resistance, increased resistance to chemicals, particularly alkalis and the enhanced dimensional stability on immersion in water already mentioned.

| Substituted Aluminum Isopropanol Derivatives Examples 10 - 21 (Parts by Weight) | | | | | | | | | | | | |
|---|---|---|---|---|---|---|---|---|---|---|---|---|
| Example | 10 | 11 | 12 | 13 | 14 | 15 | 16 | 17 | 18 | 19 | 20 | 21 |
| Aluminum ethoxyethoxide | | | | | | | | | | | | 294 |
| Aluminum Isopropoxide | 204 | 204 | 204 | 204 | 204 | 204 | 204 | 204 | 204 | 204 | | |
| Aluminum sec butoxide | | | | | | | | | | | 246 | |
| Ethoxyethanol | 90 | | | | | | | | | | | |
| Pentachlorophenol | | 177.5 | | | | | | | | | | |
| Acetic Acid | | | | | | | | | 60 | | | |
| Methacrylic Acid | | | | | | | 72 | | | | | |
| Versatic Acid | | 174 | 174 | 348 | 174 | 174 | 174 | 174 | 174 | | 174 | |
| Phthalic Anhydride | | | | | 148 | 148 | 148 | | | | 148 | |
| Maleic Anhydride | | | | | | | | 90 | 90 | | | |
| Oxo Lead Tallate | | | | | | | | | | | | 1020 |
| Dodecylbenzene Sulphonic Acid | | | | | | | | | | 326 | | |
| Isopropanol | | −55* | −110* | 149 | −55* | 77 | −55* | 147 | | | | |
| sec-Butanol | | | | | | | | | | | −70 | |
| White Spirit | | 154.5 | 119 | — | | 204 | — | | — | | | — |
| Mineral Oil | | | | | | | | 413 | | | 200 | |
| Al. Content(%) | 9.2 | 3.8 | 6.1 | 6.1 | 4.0 | 4.0 | 4.0 | 3.3 | 4.0 | 5.1 | 3.7 | 2 |

*Amount formed by reaction of aluminum isopropoxide + versatic acid and removed by distillation.

EXAMPLE 22

| Aluminum powder (leafing grade) as 67% paste in White Spirit | 150 parts by weight |
|---|---|
| Product from Example 15 | 300 parts by weight |
| Epok A1060/50 | 300 parts by weight |
| 60% Cobalt Naphthenate | 1.5 parts by weight |
| Ethyl Oxitol | 50 parts by weight |
| Isopropanol | 50 parts by weight |

The paint was made by adding the white spirit base of aluminum powder to the product solution of Example 15 and diluted with ethyl oxitol and isopropanol. The alkyd solution containing the added cobalt drier was finally added slowly while stirring to prevent local concentrations of alkyd from forming. The paint, which was readily applied by brush or sprayer, dried to a hard film which could be handled in about 30 minutes. After several days, the hardness and cohesion of the applied film had increased noticeably, but it continued to have excellent flexibility and adhesion to the substrate to which it was applied.

EXAMPLE 23

| Zinc Dust Primer | |
|---|---|
| Zinc Dust | 900 parts by weight |
| Aluminum di-isopropoxide monoversatate (Product from Example 12) | 20 parts by weight |
| Aluminum monoisopropoxide diversatate (Product from Example 13) | 40 parts by weight |
| Isopropanol | 10 parts by weight |
| Epok A1060/50 | 30 parts by weight |

After the two aluminum compounds were diluted with isopropanol, the alkyd solution was added slowly with effective stirring to prevent local excess concentrations. Finally, the zinc dust was added and the paint milled.

The resultant product could be applied satisfactorily to mild steel by brush or sprayer and dried to a hard, firmly adherent film. On immersion in water, the coated panel resisted both the immersion itself and corrosion.

EXAMPLE 24

| Zinc Phosphate Primer for Steel | |
|---|---|
| Zinc Phosphate | 100 parts |
| Rutile Titanium Dioxide | 25 parts |
| Product of Example 15 | 70 parts |
| Epok A1060/75 | 30 parts |
| Isopropanol | 30 parts |

The zinc phosphate and rutile titanium dioxide are ball-mill ground in the product of Example 15 diluted with isopropanol. After 16 hours milling, the Epok solution was added with thorough stirring to prevent excess alkyd resulting in gellation. The paint applied by brush dried quickly, but was prevented from gelling too rapidly for satisfactory application by the added isopropanol.

For spray application, more diluent could be incorporated to reduce viscosity to an acceptable level.

By brush or sprayer, recoating was possible in not more than 15 minutes. This primer proved particularly satisfactory under conditions of high condensation or water immersion.

EXAMPLE 25

| Cuprous Oxide Anti-Fouling and Anti-Corrosive Paint | |
|---|---|
| Cu₂O | 100 parts |
| Lead alumino diversatate monoisopropoxide | 40 parts |
| Product of Example 10 | 5 parts |
| Paralac IOW | 20 parts |
| Ethyl oxitol | 30 parts |
| White spirit | 30 parts |

The cuprous oxide, in a substantially dry condition, was dispersed in the mixture of ethyl oxitol and white spirit, to which the scavenger product from Example 10 had been added. After 15 minutes to complete the water scavenging, the lead alumino diversatate monoisopropoxide solution in white spirit was added to the cuprous oxide dispersion and the whole ball-milled for 16 hours. At the end of this period, the alkyd resin was slowly added to the pigment dispersion. After blending for a further half hour, the anti-fouling paint was discharged into sealed containers. The paint applied satisfactorily by brush dried in 20–30 minutes to a tackfee surface which could be repainted without pickup. Driers could be added to accelerate the after-hardening rate, but for most anti-fouling applications, this was not considered to be necessary.

EXAMPLE 26

Fungicidal Sealant for Wood

A concentrated solution was made by adding to the aluminum monoisopropoxide monoversatate monopentachlorophenate solution (Example 11), a solution of the medium long linseed alkyd marketed by I.C.I. under the trade name Paralac 10W, diluted to 50% solids content with a mixture of ethoxy ethanol, marketed by Shell Chemical under the trade name Oxitol, and white spirit, and containing sufficient cobalt drier to catalyze the normal alkyd air drying process of oxidation and polymerization, according to the following composition:

| | |
|---|---|
| Product from Example 11 | 100 parts by weight |
| Paralac 10W | 100 parts by weight |
| Oxitol | 25 parts by weight |
| White Spirit | 25 parts by weight |
| 6% Cobalt Naphthenate | 0.75 parts by weight |

This concentrate, containing 10% of pentachlorophenate, could be diluted further, preferably to about 5% pentachlorophenate content, with hydrocarbon, chlorinated hydrocarbon, a mixture thereof with alcohol such as isopropanol, butanol or Oxitol, to provide a fungicidal impregnant which restricts the passage of water into the impregnated timber.

EXAMPLE 27

Fungicidal Primer for Wood

A medium made by adding the medium/long oil length alkyd resin, Epok A1061/75, marketed by BP Chemicals International, diluted with white spirit and extended with alkali refined linseed oil to a blend of the aluminum compounds of Examples 11 and 14, was pigmented in a ball mill with a blend of pigments and fillers from which absorbed water had been scavenged by treatment with the aluminum compound of Example 10, according to the following composition:

| | |
|---|---|
| Rutile Titanium Dioxide | 39 parts by weight |
| China Clay | 12 parts by weight |
| Blanc Fixe | 129 parts by weight |
| Product from Example 10 | 5 parts by weight |
| White Spirit | 50 parts by weight |
| Product from Example 11 | 20 parts by weight |
| Product from Example 14 | 20 parts by weight |
| Epok A1061/75 | 20 parts by weight |
| Alkali Refined Linseed Oil | 20 parts by weight |
| 6% Cobalt Naphthenate | 0.2 parts by weight |

The pigments and fillers were charged to a ball mill containing the white spirit solution of the scavenger of Example 10 and such quantity of Examples 11 and 14 was desirable to ensure complete wetting and ease of mixing of the pigment. The remainder of the products from Examples 11 and 14 was then added and the paint milled until an adequate level of dispersion was effected. The blend of alkyd resin and oil containing the cobalt drier was then added with care to ensure rapid and effective dispersion with the avoidance of local concentrations of alkyd resin.

The resultant paint dries to give a flexible film effectively sealing the wood to which it was applied and providing, in addition, a considerable measure of fungicidal protection.

EXAMPLE 28

Fire Retardant Primer/Sealer for Wood

The composition detailed below employs a mixture of aluminum compounds, reacted with a medium oil length alkyd resin and diluted, both with a volatile and a non-volatile solvent, the latter being also a plasticiser for P.V.C. as a medium for the pigments and fillers and a past grade of P.V.C., which has the multiple function of stabilizing the pigment suspension, sealing pores in the coated surface, conferring flexibility by absorbing the plasticiser and acting as a halogen source in promoting fire resistance.

| | |
|---|---|
| PVC powder Breon P13Q | 100 parts by weight |
| Dioctyl phthalate | 50 parts by weight |

-continued

| | |
|---|---|
| Isopropanol | 50 parts by weight |
| Product from Example 10 | 25 parts by weight |
| Titanium Dioxide | 20 parts by weight |
| Zinc Borate -ZB 2335 | 40 parts by weight |
| Product from Example 14 | 100 parts by weight |
| Paralac 11W | 120 parts by weight |
| 6% Cobalt Naphthenate | 0.5 parts by weight |
| White Spirit | 50 parts by weight |

The titanium dioxide and zinc borate were dispersed in the isopropanol solution of Example 10 and mixed with the dioctyl phthalate, together with the PVC powder. After milling, the diluted alkyd solution containing the cobalt drier was added with thorough mixing to avoid local excess of the alkyd.

The primer/sealer was applied very easily and dried to a smooth film which remained flexible for a long time, but hardened gradually as the plasticiser was absorbed progressively by the dispersed PVC.

The dried film proved to be resistant to the passage of water and to fire.

EXAMPLE 29

The aluminum primer for wood detailed below exemplifies the beneficial reaction of the aluminum compounds with alkyd resins on the one hand and the association between actual pigments and the aluminum containing medium on the other.

| | |
|---|---|
| Product from Example 14 | 100 parts by weight |
| Beckosol P470 | 67 parts by weight |
| Alkali Refined Linseed Oil | 100 parts by weight |
| 6% Cobalt Naphthenate | 1.5 parts by weight |
| White spirit | 40 parts by weight |
| Non-leafing aluminum powder | 30 parts by weight |

To the aluminum compound, Example 14, was added with thorough stirring, the diluted alkyd resin Beckosol P470/(which is a medium/long oil length alkyd resin marketed by Synthetic Resins Limited as a 75% solution in white spirit) the alkali refined linseed oil, the cobalt drier, the rest of the white spirit and, finally, the non-leafing aluminum powder.

When applied to wood or other cellulosic surfaces, the paint dried to a strong, cohesive and adhesive film, effectively sealing the porous substrate and protecting it from the incursion of moisture and providing a suitable surface for the application of a decorative finish.

EXAMPLE 30

| White Road Marking Paint | |
|---|---|
| Titanium Dioxide | 50 parts by weight |
| Precipitated Silica Ultrasil - VN3 | 25 parts by weight |
| Isopropanol | 60 parts by weight |
| Product from Example 10 | 5 parts by weight |
| Product from Example 15 | 120 parts by weight |
| Epok A1010/50 | 30 parts by weight |

The pigment and filler preferably pre-dried were dispersed in the isopropanol solution of the water scavenger of Example 10 to remove any absorbed water; the aluminum compound of Example 15 was then added and the dispersion ball milled. When the pigment concentrate was sufficiently ground, the alkyd resin solution was added to it with careful mixing to avoid local concentrations.

The resultant paint could be applied to asphalt road surfaces without discoloration due to bleeding and dried in 10/15 minutes to a tough and durable film. It was recoatable by brush 5 minutes after application. It was observed that the applied film continued to harden on ageing for several days.

EXAMPLE 31

| Yellow Road Line Composition | |
|---|---|
| Chrome Yellow Pigment | 5 parts by weight |
| China Clay | 15 parts by weight |
| Sand | 100 parts by weight |
| Product from Example 14 | 10 parts by weight |
| Product from Example 17 | 10 parts by weight |
| Paralac 11X/60 | 10 parts by weight |
| 6% Cobalt Naphthenate | 0.1 parts by weight |

A paste of all the components was made by first dry mixing the sand, clay and chrome yellow, then adding the aluminum compound of Examples 14 and 17, followed by the alkyd resin solution Paralac 11X/60 and the cobalt drier. The slack paste was of a consistency suitable for application by doctor blade or applicator roll and at a thickness of 2 millimeters dried to a tough and adhesive marking.

EXAMPLE 32

| Cold Curing Phenol Resols/Aluminum Complex | |
|---|---|
| Cellobond J1990/60 | 100 parts by weight |
| Product from Example 19 | 50 parts by weight |

Cellobond J1990/60 is an acid curing phenol/formaldehyde resol solution in ethanol. Added to the product from Example 19, the resol is thought to form a complex with the aluminum compound through the medium of the reactive phenolic and methylol hydroxyl groups it contains. On application, atmospheric moisture brings about the replacement of isopropyl by hydroxyl groups and enables the aluminum to associate by co-ordination. The concurrent release of dodecyl benzene sulphonic acid is thought to catalyze the process of polycondensation through the associated methylol groups and convert the resin into an irreversible crosslinked complex.

The properties of the medium make it suitable for surface coating, foundry sand binding, "in situ" flooring, moulding and laminating applications.

EXAMPLE 33

| Foundry Sand Core | |
|---|---|
| Sand (Chelford 60) | 100 parts by weight |
| Powdered Phenol - Novalac/HMT blend | 2 parts by weight |
| Product from Example 10 | 1 part by weight |
| Product from Example 14 | 1 part by weight |
| Isopropanol | 1 part by weight |

The powdered novalac containing 8% of hexamethylene tetramine admixed with it, was added to the sand and dry mixed until uniform. Subsequently, the two products from Examples 10 and 14 diluted further with isopropanol, were added to the sand/novalac and mixing continued until uniform distribution of the binder on the sand had been achieved. This mix, transferred to the core mould, developed its green strength rapidly as a result of reaction between the two aluminum compounds and the reactive phenolic hydroxyl groups associated with the novalac. Subsequently, with the evaporation of the isopropanol from the sand core and the concurrent hydrolytic process resulting in coordinate association, the strength of the core increased. It could be increased further by heat treatment, which causes the HMT to convert the novalac from the thermoplastic to fully cured thermoset stage. Alternatively, this final stage could be brought about by the heat of the molten metal during the casting operation.

The same binding principle can also be used beneficially in the manufacture of grinding wheels.

EXAMPLE 34

| Black Flexographic Ink | |
|---|---|
| Furnace Black ⎫ | 10 parts by weight |
| Product from Example 14 ⎬A | 60 parts by weight |
| Isopropanol ⎭ | 20 parts by weight |
| Shellac ⎫ | 10 parts by weight |
| Isopropanol ⎬B | 10 parts by weight |

The components A were ball-milled to the requisite fineness of grind. Then the Shellac solution in isopropanol (B) was added slowly and with stirring to insure homogeneity. The resulting composite ink dried rapidly to a firmly adherent, heat resistant print, characterized by rapid solvent release, and its good "hold out" on porous surfaces and sharpness of print.

EXAMPLE 35

| Foundry Sand Core Binding Medium | |
|---|---|
| Product from Example 14 | 100 parts by weight |
| Paralac 11X/60 | 100 parts by weight |
| 6% Cobalt Naphthenate | 1 part by weight |

The binder medium was prepared by slowly adding the linseed-modified alkyd resin solution in xylene, Paralac 11X/60 containing cobalt drier, to the product from Example 14, while stirring to ensure efficient mixing. The binder medium, used at concentrations of 3% and 4% on its weight of sand (Chelford Coarse from British Industrial Sand) to make sand core test specimens for compression strengths determination. The specimens had sufficient green strength to permit their rapid ejection from the mould; and, as tabulated below, developed considerable compression strengths on ageing at atmospheric temperatures.

| Strengths (lb./sq. in.) after release from mould Binder Solution | | | | | | |
|---|---|---|---|---|---|---|
| Content | 15 mins. | 30 mins. | 1 hr. | 2 hrs. | 4 hrs. | 24 hrs. |
| 3% | 4 | 10 | 21 | 30 | 175 | 300 |
| 4% | 6 | 10 | 90 | 140 | 270 | 500 |

EXAMPLE 36

200 parts of Aroplaz 1278 alkyd resin (25% phthalic anhydride and 65% linseed oil having an acid number of 7 – 10) containing 2 parts of 6% cobalt naphthenate, was dissolved in 150 parts of aliphatic hydrocarbon and the mixture was added at room temperature with stirring to 400 parts of the product from Example 20, aluminum mono-sec-butoxide monoversatate mono half-sec-butylphthalate. The product is a low viscosity liquid suitable for use, when pigmented, as a printing ink for application by the heat set web off-set process.

Various changes and modifications of the invention can be made and, to the extent that such variations incorporate the spirit of this invention, they are intended to be included within the scope of the appended claims.

What is claimed is:

1. A storage-stable, fluid, moisturesensitive compound of a formula selected from the group consisting of

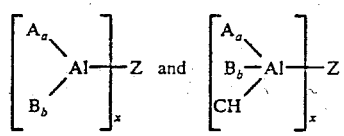

in which A, B, and C are each selected from the group consisting of alkoxy, aryloxy, alkylcarboxyl, arylcarboxyl, a dicarboxylic acid half ester moity, a dicarboxylic acid half amide moity, alkyl sulfate, aryl sulfonate, dialkyl phosphate, alkylaryl phosphate, diarylphosphate, dialkylphosphite, alkylaryl phosphite, diarylphosphite, and an oxymetal organic group of the formula OMA in which M is a divalent metal and A is as defined herein, $a$ and $b$ are each selected from 0, 1 and 2 with the proviso that $a + b = 2$, Z is a polyfunctional organic polymer or polycondensation moity derived from polymers containing at least two reactive groups selected from hydroxyl, carboxyl and hydroperoxide, and $x$ is at least 2, in which said polymers are selected from alkyd resins, phenolic resins, polyepoxides and silicone resins.

2. A compound according to claim 1 in which said A, B and C are alkyl or alkoxy-substituted alkyl of 1 to 6 carbon atoms.

3. A compound according to claim 1 in which said polymer is an alkyd resin.

4. The process for preparing a storage-stable fluid, moisture-sensitive compound of the formula of claim 1 in which a polyfunctional compound of the formula $H_xZ$ is added to an excess of an organoaluminum compound of at least one formula selected from the group consisting of

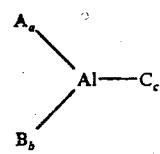

and

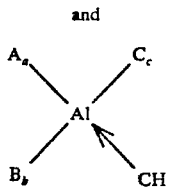

wherein A, B, C, $a$, $b$ and $x$ have the significance previously assigned, $H_xZ$ is an alkyd resin, phenolic resin, polyepoxide, or silicone resin, and $c$ is selected from 1, 2 and 3 with the proviso that $a + b + c = 3$, said $x$ being the number of groups capable of reacting with said C.

5. The process according to claim 4 in which $H_xZ$ is a alkyd resin.

6. The process according to claim 4 in which A, B, and C represent alkyl or alkoxy-substituted alkyl groups of 1 to 6 carbon atoms.

7. The process according to claim 6 in which said alkyl group is a branched chain.

8. The process according to claim 4 in which said C is selected from the group consisting of isopropoxy, sec-butoxy, and ethoxyethoxy.

9. The process according to claim 4 in which said organoaluminum compound is isopropoxy aluminum diversatate.

10. The process according to claim 4 in which said organoaluminum compound is aluminum diisopropoxide monoversatate.

11. The process according to claim 4 in which said organoaluminum compound is aluminum monoisopropoxide monoversatate mono(monoisopropyl)maleate.

12. A compound according to claim 1 in which at least one of said A and B is a versatate group.

13. A compound according to claim 1 in which at least one of said A and B is a phthalate half ester group.

14. A compound according to claim 1 in which at least one of said A and B is a maleate half ester group.

* * * * *

UNITED STATES PATENT OFFICE
CERTIFICATE OF CORRECTION

Patent No. 4,075,178          Dated February 21, 1978

Inventor(s) John Harry Wallice Turner

It is certified that error appears in the above-identified patent and that said Letters Patent are hereby corrected as shown below:

In the ABSTRACT, delete "z" and add --Z--

In Column 6, line 42, delete "of water" and add --of free water--

In Column 14, line 61, delete "past" and add --paste--

Signed and Sealed this

Sixth Day of June 1978

[SEAL]

Attest:

RUTH C. MASON
*Attesting Officer*

DONALD W. BANNER
*Commissioner of Patents and Trademarks*